United States Patent [19]

Guess et al.

[11] Patent Number: 5,069,664
[45] Date of Patent: Dec. 3, 1991

[54] INTRAVASCULAR ULTRASONIC ANGIOPLASTY PROBE

[75] Inventors: Joe F. Guess, Estes Park, Colo.; Paul J. Zalesky, Huntington Beach, Calif.

[73] Assignee: Inter Therapy, Inc., Costa Mesa, Calif.

[21] Appl. No.: 469,770

[22] Filed: Jan. 25, 1990

[51] Int. Cl.⁵ .............................................. A61B 17/32
[52] U.S. Cl. ..................... 604/22; 128/660.06; 128/24 R
[58] Field of Search ........... 128/24 R, 660.03, 662.06; 604/22

[56] References Cited

U.S. PATENT DOCUMENTS

| | | |
|---|---|---|
| 3,352,303 | 7/1965 | Delaney . |
| 3,565,062 | 2/1971 | Kurtis ..................... 128/24 |
| 3,942,122 | 4/1974 | Jones ..................... 128/24 A |
| 4,063,557 | 12/1977 | Wuchinich et al. ........ 128/276 |
| 4,223,676 | 9/1980 | Wuchinich et al. ........ 128/276 |
| 4,504,264 | 3/1985 | Kelman ..................... 604/22 |
| 4,516,398 | 6/1984 | Wuchinich ................ 604/22 |
| 4,535,759 | 8/1985 | Polk et al. .............. 128/24 A |
| 4,561,438 | 12/1985 | Bonnet et al. ............ 128/328 |
| 4,634,419 | 1/1987 | Kreizman et al. .......... 604/22 |
| 4,698,058 | 10/1987 | Greenfeld et al. ......... 604/266 |
| 4,750,902 | 6/1988 | Wuchinich et al. ........ 128/24 AA |
| 4,751,916 | 6/1988 | Bory ..................... 128/24 A |
| 4,794,931 | 1/1989 | Yock ..................... 128/660.03 |
| 4,804,364 | 2/1989 | Dieras et al. ............ 604/22 |
| 4,808,153 | 2/1989 | Parisi ..................... 604/22 |
| 4,816,018 | 3/1989 | Parisi ..................... 604/22 |
| 4,861,332 | 11/1989 | Parisi ..................... 604/22 |
| 4,886,060 | 12/1989 | Wiksell ................... 604/22 |
| 4,920,954 | 5/1990 | Alliger et al. ........... 272/24 AA |
| 4,936,281 | 6/1990 | Stasz ..................... 604/22 |
| 4,950,277 | 8/1990 | Farr ..................... 604/22 |
| 4,962,755 | 10/1990 | King et al. .............. 604/22 |
| 4,970,581 | 12/1990 | Wiksell ................... 604/22 |

Primary Examiner—Richard J. Apley
Assistant Examiner—L. Thomas
Attorney, Agent, or Firm—Nixon & Vanderhye

[57] ABSTRACT

A probe for ultrasonically removing unwanted biological material, for example, from a vessel in a patient's cardiovascular system, includes a catheter assembly having distal and proximal catheter sections, each defining a respective lumen. A subassembly is connected to and between these catheter sections and houses piezoceramic transducer elements which are adapted to vibrate at ultrasonic frequencies. An elongate flexible working element (e.g., one or more wire elements) is housed within the distal catheter section and projects beyond that section's distal end so as to be adapted to contact unwanted biological material. The proximal end of the working element is coupled to the transducer elements via ultrasonic coupling structures so as to responsively vibrate at ultrasonic frequencies. The subassembly also defines an aspiration channel which fluid-connects the lumens of the proximal and distal catheter sections so that unwanted biological material removed by the ultrasonically vibrated working element may be aspirated to a patient-external specimen collection site.

18 Claims, 3 Drawing Sheets

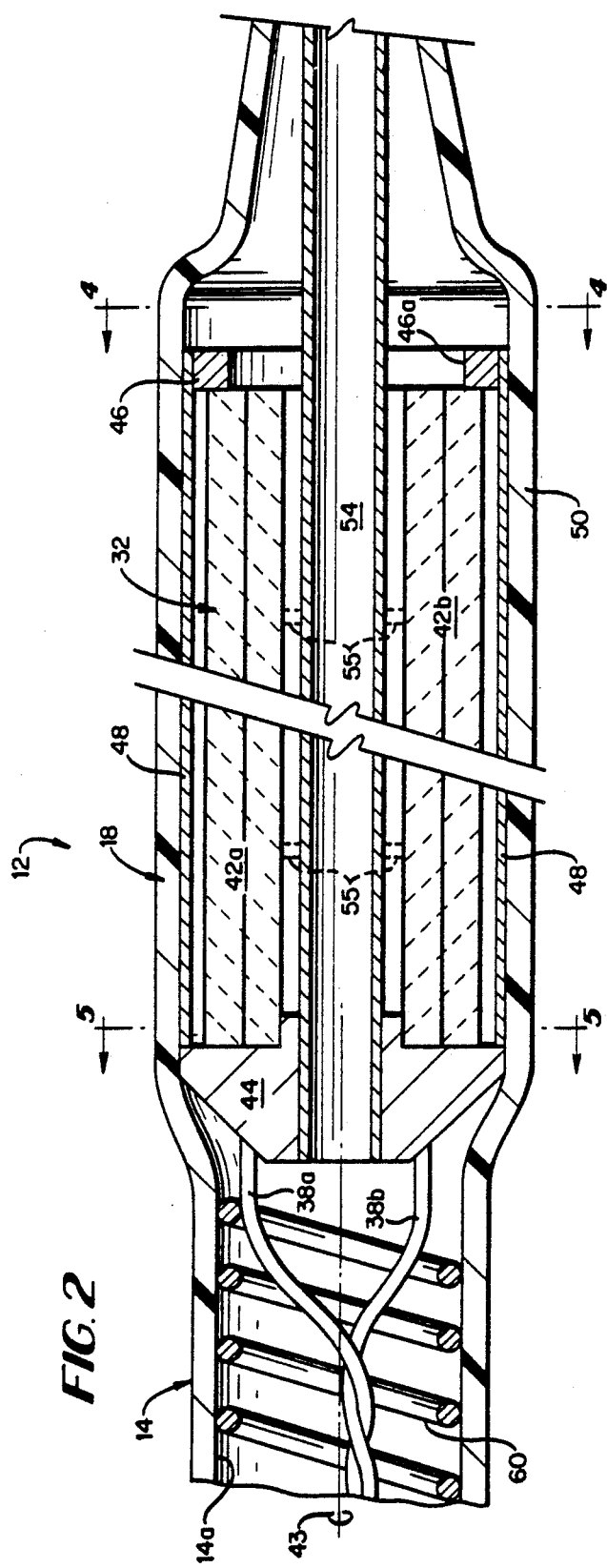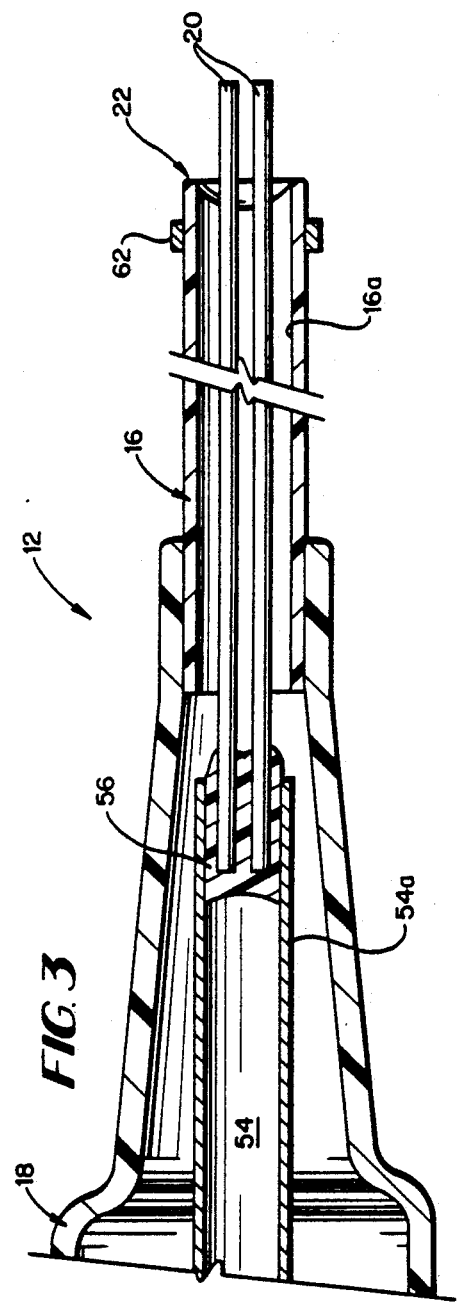

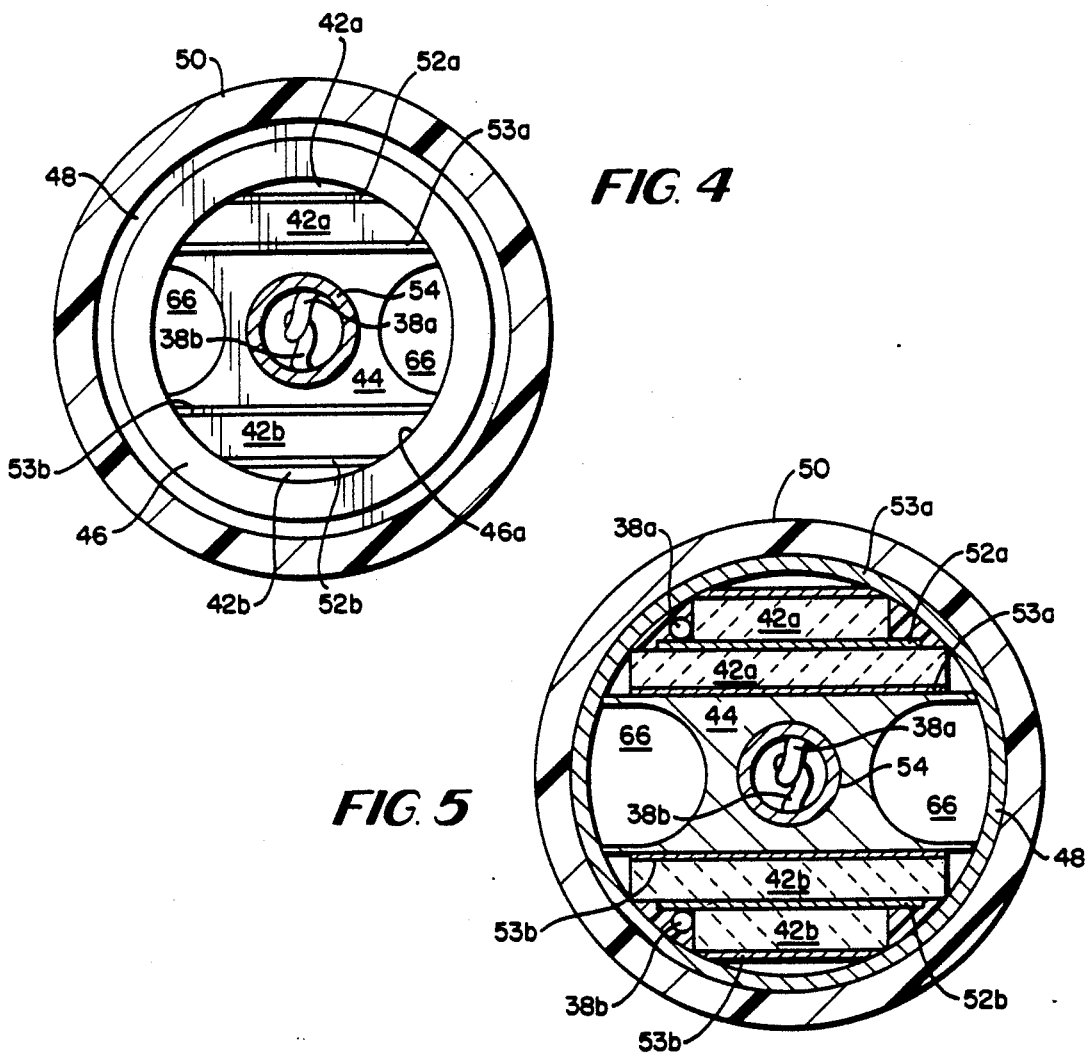
FIG. 4
FIG. 5
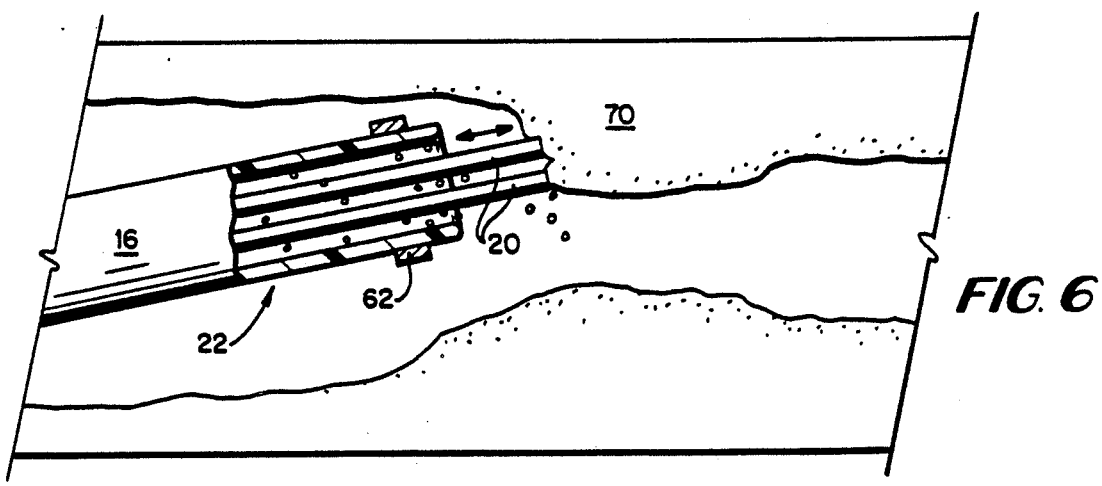
FIG. 6

INTRAVASCULAR ULTRASONIC ANGIOPLASTY PROBE

FIELD OF INVENTION

This invention generally relates to the field of therapeutic medical probes. More specifically, the present invention relates to probe assemblies especially adapted for use within a patient's cardiovascular system so as to remove obstructions and/or lesions therefrom. In preferred forms, the invention is embodied in an intravascular probe assembly having distally and proximally extending catheter portions, and a subassembly which houses an ultrasonic transducer connected to and between these catheter portions. An operative wire element extends from the subassembly (where it is operatively associated with the transducer) within the distally extending catheter portion, and terminates in a tip adapted to being brought into contact with unwanted biological material (e.g., arterial obstructions, lesions, plaque, etcetera). Ultrasonic vibration of the transducer (which may be activated by patient-external driver means) will therefore responsively cause the wire element to vibrate ultrasonically to thereby remove the unwanted biological material in contact with the wire's tip.

BACKGROUND AND SUMMARY OF THE INVENTION

A. Summary of Prior Art And Information Disclosure Statement

Therapeutic medical devices involving the use of ultrasonic acoustics for the removal of unwanted material from bodily tissue are well known. For example, U.S. Pat. No. 4,808,153 to Parisi suggests that a number of longitudinally vibratory crystals may be mounted in the distal end of an arterial probe. These crystals are secured within a socket of a hollow, beveled-edge tip (which serves as the working element of the probe) so that the vibratory crystals are flush with the tip's outer surface. In use, the entire probe, including the tip containing the vibratory crystals, is inserted into an artery and then moved along the wall of the artery. The vibrating tip therefore emulsifies plaque on the artery's interior wall which is then removed to a patient-external location by vacuum.

U.S. Pat. No. 3,941,122 to Jones discloses a therapeutic ultrasonic probe adapted for use in ophthalmic operations. The end of the probe of Jones '122 consists of a piezoceramic disc which serves to break up the unwanted biological material, which is then aspirated through the probe.

U.S. Pat. No. 3,565,062 to Kuris, and U.S. Pat. No. 4,698,058 to Greenfield et al, both disclose therapeutic ultrasonic probes whereby the piezoceramic elements are located physically outside of the patient during use. Kuris '062 utilizes a tubular member to couple the ultrasonically vibrated piezoceramic element to a distally located working element. Greenfield et al '058, on the other hand, discloses an ultrasonically vibratory wire element.

Attention is also directed to the following U.S. patents which generally disclose therapeutic medical probes using ultrasonic energy whereby a piezoceramic transducer element is located physically outside of the patient during use: U.S. Pat. No. 4,535,759 to Polk et al, U.S. Pat. No. 4,516,398 to Wuchinich et al, U.S. Pat. No. 4,504,264 to Kelman, U.S. Pat. No. 4,063,557 to Wuchinich et al, U.S. Pat. No. 3,352,303 to Delaney, U.S. Pat. No. 4,816,018 to Parisi, U.S. Pat. No. 4,751,916 to Bory, U.S. Pat. No. 4,794,931 to Yock, U.S. Pat. No. 4,561,438 to Bonnett et al, and U.S. Pat. No. 4,223,676 to Wuchinich et al.

B. Summary of the Invention

The present invention is broadly embodied in a therapeutic medical probe having a piezoceramic transducer operatively coupled to a vibratory wire element. More specifically, the invention includes novel coupling structures which serve to acoustically couple the piezoceramic transducer and the wire element. The novel coupling structures of this invention more readily allow for miniaturization of the transducer subassembly by about one-half in length as compared to conventional ultrasonic angioplasty devices, while serving to amplify the vibratory motion of the piezoceramic transducer that is transferred to the wire element so that more effective therapeutic treatment can be realized. In this regard, it is believed that the acoustic structure provided by means of the present invention not only effectively amplifies the vibratory displacement of the piezoceramic transducers, but also effectively isolates these vibratory displacements so as to direct substantially all acoustic energy towards the wire element to thus achieve maximum vibratory displacements of the same (thereby increasing the efficiencies for a given miniaturized transducer size.)

The present invention is most preferably embodied in an ultrasonic angioplasty probe which includes a catheter of sufficiently small size so as to be placed within a vessel of a patient's vascular system. The catheter includes proximally and distally extending catheter sections, and a generally tubular subassembly section which is interposed between and connected to these proximally and distally extending catheter sections. The tubular subassembly houses piezoceramic transducers which are adapted to vibrate at ultrasonic frequencies in response to receiving suitable electrical stimulus.

The subassembly also houses an ultrasonic horn which acoustically couples the ultrasonic vibratory motion of the piezoceramic elements to at least one distally extending wire element housed within the distally extending catheter section. The wire element projects beyond the terminal end of the distally extending catheter section by a preselected dimension to provide a tip that is adapted to contact plaque deposits and/or unwanted biological material within the patient's vascular system.

At least one longitudinal aspiration channel which fluid-connects the lumens of the proximally and distally extending catheter sections is defined within the transducer subassembly to thereby allow aspiration (as by means of a vacuum source connected to the proximally extending catheter section externally of a patient) of unwanted biological material removed via the ultrasonically vibrated wire element. In this regard, the material is aspirated into the annular space surrounding the wire element, flows to the aspiration channel of the subassembly, and then is withdrawn via the lumen of the proximally extending catheter section.

Other aspects and/or advantages of this invention will become more clear after careful consideration is given to the following detailed description of the preferred exemplary embodiments.

BRIEF DESCRIPTION OF THE ACCOMPANYING DRAWINGS

Reference will hereinafter be made to the accompanying drawings wherein like reference numerals throughout the various FIGURES denote like structural elements, and wherein;

FIG. 2 is a detailed longitudinal cross-sectional view of the distally located transducer housing associated with the angioplasty probe of this invention;

FIG. 3 is a detailed longitudinal cross-sectional view of the distal terminal end of the angioplasty probe of this invention;

FIG. 4 is a cross-sectional view of the transducer housing depicted in FIG. 2 as taken along line 4—4 therein;

FIG. 5 is another cross-sectional view of the transducer housing depicted in FIG. 2 as taken along line 5—5 therein; and FIG. 6 is a schematic representation of the distal end of the angioplasty probe of this invention during use.

DESCRIPTION OF THE PREFERRED EXEMPLARY EMBODIMENTS

Figure 1:
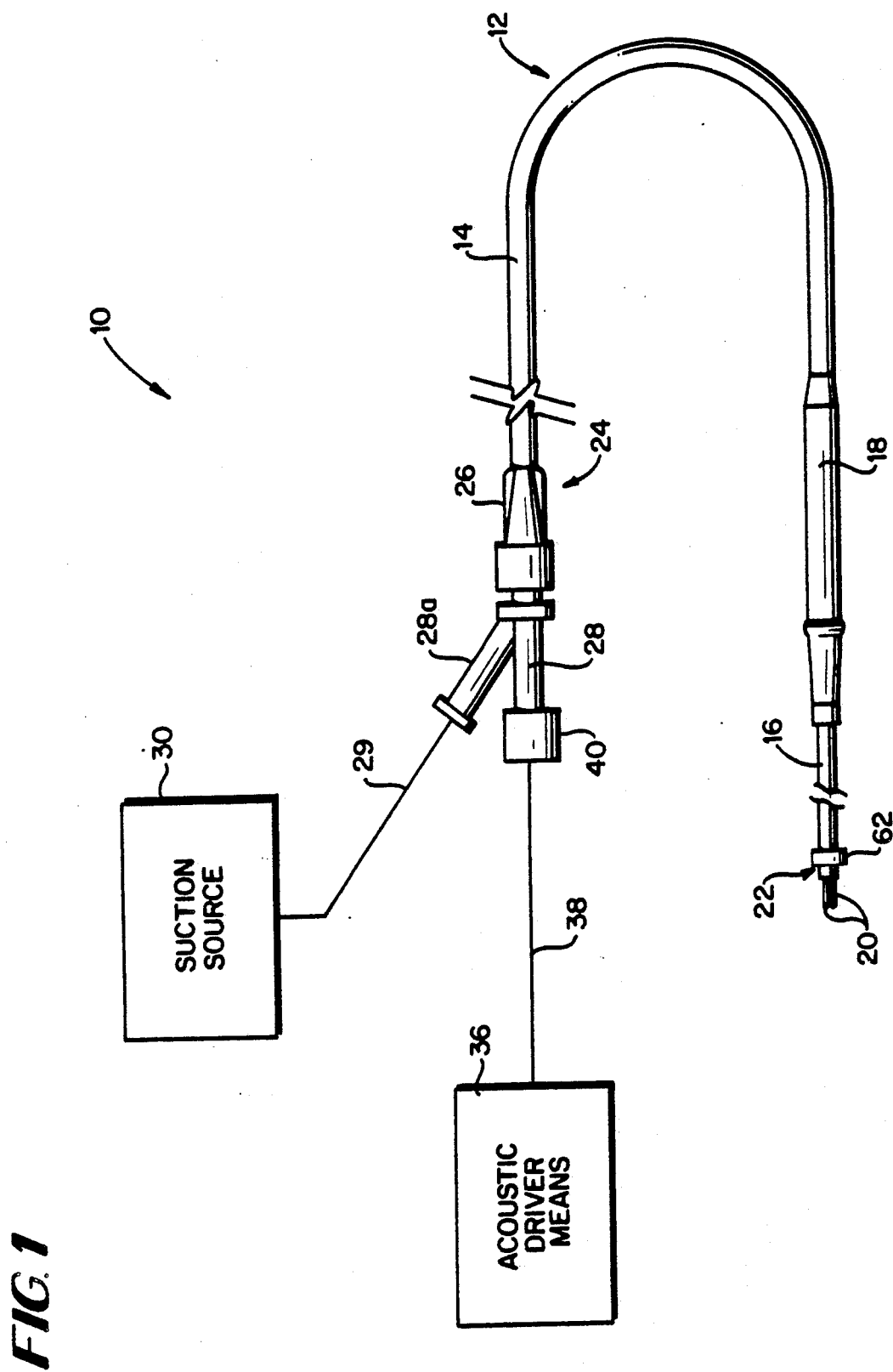
FIG. 1 is a schematic diagram of an intravascular angioplasty system which includes the ultrasonic angioplasty probe of the present invention.

A preferred system 10 according to the present invention includes a probe assembly 12 sized and configured so as to be insertable within a patient's cardiovascular system. The probe 12 is generally comprised of proximal and distal catheter sections 14, 16, respectively, and a generally tubular transducer subassembly section 18.

A pair of flexible wire elements 20 extend beyond the terminal end 22 of the probe 12 and are thereby adapted to be brought into contact with arterial plaque and/or other unwanted biological material within a patient's cardiovascular system. As will be explained in greater detail below, the wire elements are caused to be vibrated at ultrasonic frequencies (essentially entirely in a longitudinal direction), and it is this vibratory motion that removes arterial plaque and/or other unwanted biological material from the walls of a vessel within a patient's cardiovascular system.

The proximal (and patient-external) end 24 of probe 12 includes a conventional Leur connector 26 to which a side-arm connector 28 may be coupled. The side arm 28a of connector 28 is coupled operatively via line 29 to a suction source 30 which provides a means of aspirating removed arterial plaque and/or other unwanted biological material through the probe 12 and on to a collection site external of the patient (not shown).

Electrical impulse signals to excite the piezoceramic transducer means 32 (see FIG. 2, for example) are generated via acoustic driver means 36 coupled operatively to the transducers 32 by any suitable cabling means 38, for example, a twisted wire pair. It will be appreciated that the cable means 38 is housed within the probe 12 and is directed to the acoustic driver means 36 through the connector 28. In this regard, the connection will have a suitable seal cap 40 through which the cable means 38 extends so as to seal the connector 28 against fluid leakage.

FIGS. 2-3 are enlarged, cross-sectional views of the probe assembly 12 which more particularly depict the internal structures associated with the transducer subassembly 18.

As is perhaps more clearly seen in FIG. 2, the transducer subassembly 12 houses piezoceramic transducer means 32, which in the preferred embodiment, is in the form of diametrically opposing pairs of piezoceramic wafers 42a, 42b. The wafers 42a, 42b are most preferably constructed of lead zirconate-lead titanate ceramic material, but other ceramic materials which exhibit piezoelectric properties, such as PZT-4, PZT-8 or like "driver" ceramic materials, may certainly be employed in the practice of the present invention. Thus, the particular material from which the wafers 42a, 42b are made is not critical, provided it is capable of vibrating at ultrasonic frequencies and at high stress levels in response to an electrical stimulus provided by acoustic driver means 36 (see FIG. 1).

The piezoceramic wafer pairs 42a, 42b have their lengthwise dimension oriented essentially parallel to the longitudinal axis 43 of the generally tubular subassembly 12. In this regard, the proximal ends of piezoceramic wafer pairs 42a, 42b are rigidly connected (e.g., via suitable epoxy) to a coupling member 44 (see also FIG. 4). Although not essential, the distal ends of the piezoceramic wafer pairs 42a, 42b are preferably rigidly coupled to an annular mounting disc 46. The piezoceramic wafer pairs 42a, 42b are, moreover, surrounded by a metallic tubular shield 48 which provides electrical shielding functions to the transducer means 34 during use. In this regard, the shield 48 is preferably coupled operatively to a coiled shield/ground wire 60 housed within the proximal catheter section 14.

The entire subassembly 18 is surrounded with an electrically insulating sheath 50 which preferably is integral with the proximal catheter section 14. It will be appreciated that the diameter of the subassembly 18 is somewhat larger than the diameters of the proximal and distal catheter sections 14, 16, respectively, due to the spatial requirements needed to accommodate the transducer means 32.

As is more clearly shown in FIG. 5, the piezoceramic wafers in each of the pairs 42a, 42b, are separated by a metallized face 52a, 52b, respectively, which serves as a high potential electrode for the same. This metallized face 52a, 52b is electrically connected (e.g., via soldering) to respective ones of wires 38a, 38b, forming the cable means 38. It will be understood that the wires 38a, 38b are electrically insulated and thus have a portion of that insulation removed in the vicinity of metallized faces 52a, 52b to permit the latter to be electrically coupled to the former. Metallized faces 53a and 53b serve as ground electrodes for the piezoceramic wafers.

Important to the present invention is the presence within the subassembly 18 of acoustic horn element 54. As is seen in FIG. 2, the horn element 54 is rigidly and concentrically affixed at its proximal end to the coupling member 44 by suitable means. In this regard, the horn element 54 is most preferably fixed to coupling member 44 by means of a suitable epoxy which is preferably "loaded" (i.e., blended) with a strength enhancing filler material (e.g., alumina particles). The horn element 54 extends distally from the coupling member 44 in the space defined between the piezoceramic wafer pairs 42a, 42b. Thus, the horn element 54 is positioned between and substantially parallel to the piezoceramic wafer pairs 42a, 42b.

The horn element 54 serves an additional beneficial function of amplifying the vibratory displacements of the piezoceramic wafers, which results in greater vibratory displacements of wire elements 20 connected to the distal end of the horn element 54 (see FIG. 3). In this regard, the horn element may be constructed of a material (e.g., stainless steel or titanium) that is inherently capable of withstanding significantly greater vibratory stress as compared to the piezoceramic wafers 42a, 42b. For this reason, the diameter (cross-sectional area) of the horn element 54 may be significantly smaller than the cross-sectional area of the piezoceramic wafers 42a, 42b, thereby resulting in an increased vibratory displacement occurring at the tip of wire elements 20 as compared to the vibratory displacements of the wafers 42a, 42b per se.

The length of the horn element 54 will be determined in large part by the acoustic propagation speed in the material from which each of the horn element 54 and the wafers 42a, 42b are constructed. For example, when using stainless steel as the material from which the horn element 54 is constructed, and lead zirconate-lead titanate as the material from which the wafers 42a, 42b are constructed, the horn element 54 will be about 1.6 times the length of the wafers 42a, 42b due to the differences in the sound propagation velocities as between these materials.

The horn element 54 is preferably unsupported along substantially its entire length (i.e., is only supported via the rigid connection between the proximal end of horn element 54 and the coupling member 44) and thus terminates in a free (unsupported) distal end 54a as is shown in FIG. 3. If the mounting disc 46 is employed, it is necessary that its central aperture 46a (see FIG. 4) be of sufficiently large size so as to provide adequate clearance with the horn element 54 so that the disc 46 does not interfere with (e.g., damp) the longitudinal vibratory movements of the horn and/or impede the aspiration of removed tissue into and through the channels 66.

In some instances, however, it may be beneficial to provide some support along the axial length of the horn element 54 which permits axial displacements to occur, but prevents the occurrence of lateral displacements (i.e., so that the longitudinal vibrational motion of the horn will not be significantly impaired). In this regard, one or more thin diaphragms or flexural members (noted by dashed lines schematically in FIG. 2 by reference numeral 55) may be provided along the axial length of the horn element 54.

The rigid connection between the coupling member 44 and the proximal end of the horn 54 is established at a vibratory node (i.e., a location where minimal or essentially zero vibratory displacements occur) position, whereas the distal ends of the piezoceramic wafer pairs 42a, 42b are located at a vibratory antinode (i.e., a position where maximum vibratory displacements occur. In addition, the unconnected distal ends of the horn 54 and the piezoceramic wafer pairs 42a, 42b are out-of-phase with one another—that is, when one of the distal ends of the horn 54 or the piezoceramic wafer pairs 42a, 42b is at a point of maximum vibratory displacements in one direction, the other of the distal ends of the horn 54 or the piezoceramic wafer pairs 42a, 42b is at a point of maximum vibratory displacements in an opposite direction.

Due to the fact that the horn element 54 is preferably much smaller in mass as compared to the piezoceramic wafers 42a, 42b, the vibratory node must be very near the proximal end of the horn element 54 in order to have the mechanical impedance of the horn-wire system equal to the more massive (relatively) piezoceramic wafers 42a, 42b. Thus, the dimensions of the horn element 54/wire element 20 components will largely determine the operational frequency of vibration. In this regard, one skilled in this art can select the precise dimensions of the operative components—i.e., the piezoceramic element(s), horn element, and wire element(s)—in order to arrive at an optimal vibration frequency of operation for given end use applications. The length of the piezoceramic wafers can, however, be selected to be between less than about one-quarter wavelength to nearly one-half wavelength at a typical operating frequency of between 20 to 40 KHz.

According to the present invention, therefore, a maximum of vibratory energy is transferred to the wire elements 20 since any vibration interference that may occur as between the piezoceramic wafer pairs 42a, 42b and the horn 54 is negligible and/or since the displacements of the piezoceramic wafer pairs 42a, 42b is amplified. Thus, minimal energy loss and an efficient concentration of vibrational energy occurs at the wire elements.

In addition, it will be appreciated that, since the proximal ends of the piezoceramic wafer pairs 42a, 42b and the horn 54 are located at a vibratory node, then minimal vibratory energy is transferred to the catheter sections 14 and/or 16. This functional attribute of the invention thereby ensures that the catheter sections 14 and/or 16 are essentially isolated from vibratory displacements.

As is seen more clearly in FIG. 3, the proximal ends of the flexible wire elements 20 are rigidly coupled to the distal end 54a of horn 54 by means of, for example, epoxy (shown schematically in FIG. 3 by reference numeral 56). Thus, the longitudinal vibratory movements of the horn element 54 (induced by the transducer means 34 as discussed previously) are transferred to these wire elements 20 so that the distal ends thereof that extend beyond the terminal end 22 of distal catheter 16 are capable of removing arterial plaque and/or other unwanted biological material that they contact. It should be understood that although a pair of wire elements 20 just happens to be shown in the accompanying FIGURES, a single wire element or more than a pair of wire elements may be used, if desired.

In use, the probe assembly 12 may be inserted percutaneously into a preselected vessel (e.g., femoral artery) associated with a patient's cardiovascular system. In this regard, movements of the probe assembly 12 may be visually monitored by the attending physician by observing the location of a marker band 62 formed of a fluoroscopically visible material (e.g., gold) using conventional fluoroscopic imaging technique.

The physician manipulates and guides the probe assembly 12 until the exposed distal ends of the wire elements 20 reach the location of the arterial plaque 70 to be removed from the vessel 72. It will be appreciated that the location of the arterial plaque 70 can be "mapped" in advance using intravascular imaging techniques, such as disclosed in commonly owned and copending U.S. application Ser. No. 07/395,839 filed on Aug. 18, 1989 in the name of James M. Griffith et al entitled "Intravascular Ultrasonic Imaging Probe and Methods of Using Same" (the entire content of which is expressly incorporated by reference herein). When the wire elements 20 are properly positioned, the physician may then activate the acoustic driver means 36 so as to responsively cause the flexible wire elements 20 to vibrate at ultrasonic frequencies as has been described in detail above.

The reciprocal longitudinal ultrasonic vibratory motion of the wire elements 20 will thereby comminute the plaque 70, which may then be aspirated into the lumen 16a defined by the distal catheter section 16 by means of the patient-external suction source 30 (see FIG. 1). In this regard, fluid communication between the lumen 14a defined by the proximal catheter section 14 and the lumen 16c defined by the distal catheter section 16 is established by means of aspiration channels 66 formed in the coupling member 44 (see FIG. 5). Thus, removed plaque is aspirated into the lumen 14a of the proximal catheter section 14 via these channels 66 where it can then proceed externally of the patient to a specimen collection site (not shown). Once a sufficient amount of the plaque 70 has been removed, the acoustic driver means 36 is disabled so that the probe assembly 12 may be removed from, or repositioned within, the patient's cardiovascular system.

As will now undoubtedly be appreciated, the present invention is embodied in novel structures which function in an equally novel manner. However, the preferred embodiment discussed above should be considered as exemplary only. Thus, while the present invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An probe for ultrasonically removing unwanted biological tissue comprising an elongate probe assembly having proximal and distal end portions, and a transducer subassembly located near said distal end portion of said probe assembly, wherein said transducer subassembly includes:
    transducer means having a predetermined length dimension and adapted to vibrate at ultrasonic frequencies in response to electrical driving signals;
    elongate ultrasonic horn means positioned laterally adjacent to said transducer means and aligned substantially parallel to said length dimension thereof;
    coupling means rigidly coupling the proximal ends of said transducer means and said ultrasonic horn means one to another so as to allow said vibratory displacements of said transducer means to be transferred to said horn means; and
    flexible wire means operatively connected to and distally extending from said horn means so that said vibratory displacements of said horn means are responsively transferred to said wire means, wherein said wire means includes a terminal end portion adapted to contact said unwanted biological tissue and to remove the same by means of said responsive vibratory displacements thereof.

2. A probe assembly for removing unwanted biological tissue comprising an elongate probe assembly which includes a distally located transducer subassembly, said transducer subassembly including:
    ultrasonic transducer means having proximal and distal ends, said transducer means undergoing vibratory displacements at ultrasonic frequencies in response to receiving an electrical stimulus;
    ultrasonic horn means having proximal and distal ends and positioned laterally adjacent and parallel to said transducer means; and
    coupling means, which is located essentially at a node position whereby minimum vibratory displacements occur, for rigidly coupling said proximal end of said transducer means to said proximal end of said horn means so that said proximal ends of said transducer means and said horn means are likewise located essentially at said node position; wherein
    said distal ends of said transducer means and said horn means are unconnected to one another and are each located at an antinode portion whereby maximum vibratory displacements occur, and wherein
    said vibratory displacement of said horn means distal end is out of phase with said vibratory displacement of said transducer means distal end such that when one of said distal ends is displaced to a maximum extent in one direction, the other of said distal ends is displaced to a maximum extent in an opposite direction; and wherein
    said probe assembly further includes working element means operatively coupled to said horn means distal end for responsive vibratory displacements therewith.

3. A probe for ultrasonically removing unwanted biological material from a vessel in a patient's vascular system comprising a catheter assembly which is sized and configured to be inserted within the vessel of a patient's vascular system containing the unwanted biological material, said catheter assembly including:
    (i) distal and proximal extending catheter sections each defining a respective lumen;
    (ii) a subassembly connected to and between said distally and proximally extending catheter sections;
    (iii) an elongate working element housed within said distal catheter section and having a proximal end located adjacent said subassembly and a distal end which is exposed beyond a terminal end of said distal catheter section;
    (iv) said subassembly including (a) transducer means having a pair of transducer elements adapted which are laterally separated relative to a longitudinal direction of the catheter assembly so as to establish a longitudinal space therebetween, said pair of transducer elements adapted to vibrate at ultrasonic frequencies in response to electrical driving signals, (b) means for coupling said ultrasonic vibration of said transducer means to said working element so that said working element responsively vibrates at ultrasonic frequencies, said means for coupling including an ultrasonic horn disposed in said space between said pair of transducer elements and oriented substantially parallel thereto, and (c) means establishing an aspiration channel longitudinally through said subassembly so as to fluid-connect the lumens of said proximally and distally extending catheter sections.

4. A probe as in any one of claim 1-3, wherein said transducer means comprises diametrically opposed sets piezoelectric transducer elements.

5. A probe as in claim 3, wherein said working element includes at least one elongate flexible wire element.

6. A probe as in claim 3, wherein said coupling means includes an elongate horn element.

7. A probe as in claim 6, wherein said coupling means includes acoustic coupling means operatively connected to said horn element for acoustically coupling said horn element and said transducer means.

8. A probe as in claim 7, wherein said horn element has one end rigidly fixed to said coupling means and another end opposite to said one end, said horn element being unsupported along its length between said one and another ends.

9. A probe as in claim 7, wherein said horn element has one end rigidly fixed to said coupling means and another end opposite to said one end, and including means for supporting an axial length of said horn element between said one and another ends thereof.

10. A medical probe assembly for removing selected tissue, comprising:
a catheter defining a catheter lumen;
transducer means positioned at a distal end portion of said catheter and oriented along a length-wise dimension of said catheter, said transducer being capable of vibratory movements at ultrasonic frequencies in response to receiving an electrical stimulus;
a flexible working element extending distally relative to said transducer means; and
coupling means for transferring said ultrasonic vibratory movements of said transducer means to said flexible working element; wherein said coupling means includes
(i) an elongate horn element positioned laterally adjacent and parallel to said transducer means; and
(ii) acoustic coupling means for acoustically coupling said horn element and said transducer means to transfer vibratory movements of said transducer means to said horn element.

11. A probe assembly as in claim 10, wherein said horn element has one end rigidly fixed to said coupling means and another unsupported end opposite to said one end.

12. A medical probe assembly for removing selected tissue, comprising:
a catheter defining a catheter lumen;
transducer means having a pair of laterally separated transducer elements positioned at a distal end portion of said catheter and oriented in a lengthwise direction of said catheter, said transducer being capable of vibratory movements at ultrasonic frequencies in reponse to receiving an electrical stimulus;
a flexible working element extending distally relative to said transducer means; and
coupling means for (i) coupling said vibratory movements of said transducer means to said flexible working element, and (ii) amplifying the magnitude of said ultrasonic vibratory movements of said transducer means to produce a relatively greater magnitude of vibratory movement of said flexible working element wherein said coupling means includes,
an elongate horn element positioned laterally adjacent and parallel to said transducer means between said laterally separated transducer elements, and
acoustic coupling means for acoustically coupling said horn element and said transducer means for vibration in a longitudinal direction, wherein
said horn element has an end rigidly fixed to said coupling means and an unsupported end opposite to said fixed end, said horn element being unsupported along its length between said fixed and unsupported ends.

13. A probe assembly as in claim 12, wherein said transducer means includes diametrically opposed sets of transducer elements.

14. An axially elongate medical probe assembly for removing selected tissue, comprising:
a catheter defining a catheter lumen;
transducer means located at a distal portion of said catheter and adapted to vibrate at ultrasonic frequencies in response to receiving an electrical stimulus;
at least one flexible wire working element; and
coupling means for acoustically coupling said transducer means and said working element, said coupling means including acoustic horn means having one end operatively coupled to said transducer means and an opposite end operatively coupled to said working element, wherein
said transducer means including (i) a diametrically opposed, laterally separated set of transducer elements axially oriented relative to said catheter, (ii) an annular rigid disc positioned in axially spaced relation to said coupling means, (iii) said set of transducers being positionally fixed between said coupling means and said rigid disc so as to maintain said lateral separation of said set of transducer elements, and (iv) a horn element having a proximal end operatively coupled to said coupling means and extending distally therefrom so as to be disposed between said laterally separated set of transducer elements.

15. An intravascular probe for removing arterial obstructions, comprising in combination:
an elongate catheter defining a catheter lumen;
said catheter including a distally positioned subassembly adapted to being inserted into a patient's vascular system, said subassembly establishing distal (and proximal catheter portions having respective distal and) proximal lumens;
said subassembly including (i) an ultrasonic transducer comprised of diametrically opposed and laterally separated sets of piezoelectric ceramic elements, (ii) means defining at least one channel which fluid-connects said distal and proximal lumens to allow fluid to flow through said subassembly between said laterally separated sets of piezoelectric ceramic elements, and (iii) an ultrasonic horn element positioned between said diametrically opposed and laterally separated sets of piezoelectric ceramic elements;
at least one flexible wire element disposed within said distal lumen and having a terminal end adapted to contact an arterial obstruction; and
means for acoustically coupling said ultrasonic transducer and said at least one flexible wire element so as to transfer ultrasonic vibrations of said transducer to said wire element, whereby said vibrating wire element is adapted to remove arterial obstructions.

16. A probe as in claim 15, wherein said acoustic coupling means further includes an elongate horn element operatively coupled to and positioned between sets of piezoelectric ceramic elements at one end thereof, wherein said flexible wire element is secured to an opposite end thereof.

17. A system for removing intravascular obstructions comprising:
a probe assembly which includes, (i) distal and proximal catheter portions each defining distal and proximal catheter lumens, respectively;

(ii) a subassembly connected to and between said distal and proximal catheter portions, said subassembly housing a pair of laterally separated ultrasonic transducer elements, said subassembly defining an aspiration channel which fluid-connects said distal and proximal catheter lumens and allows fluid to flow through said subassembly between said pair of laterally separated transducer elements, and a ultrasonic horn element positioned between said pair of laterally separated transducer elements;

(iii) at least one elongate wire element connected to said horn element and extending from said subassembly within said distal catheter portion, said wire element having a proximal end in operative association with said transducer so as to be responsively vibrated ultrasonically by means of said transducer, and a distal end adapted to contact said intravascular obstruction, whereby ultrasonic vibration of said wire element removes at least a portion of said obstruction in contact with said wire element distal end;

said system further comprising, ultrasonic driver means operatively coupled to said transducer for causing said transducer to vibrate ultrasonically; and aspiration means in fluid communication with said proximal catheter lumen for aspirating said removed obstruction portion sequentially through said distal catheter lumen, said subassembly via said aspiration channel and said proximal catheter lumen to a patient-external collection site.

18. A system as in claim 17, wherein said piezoceramic transducer comprises diametrically opposed sets of piezoelectric crystal elements positionally fixed within said subassembly.

* * * * *